United States Patent [19]

Nudelman

[11] Patent Number: 4,938,205

[45] Date of Patent: Jul. 3, 1990

[54] ENDOSCOPE WITH TRACED RASTER AND ELEMENTAL PHOTODETECTORS

[75] Inventor: Sol Nudelman, Avon, Conn.

[73] Assignee: The University of Connecticut, Farmington, Conn.

[21] Appl. No.: 199,997

[22] Filed: May 27, 1988

[51] Int. Cl.⁵ .............................................. A61B 1/06
[52] U.S. Cl. .................................... 128/6; 606/14; 606/16
[58] Field of Search .................. 128/6, 303.1, 395–398

[56] References Cited

U.S. PATENT DOCUMENTS

| | | | |
|---|---|---|---|
| 2,922,844 | 1/1960 | Sheldon | 358/98 |
| 3,021,834 | 2/1962 | Sheldon | 358/98 |
| 3,499,107 | 3/1970 | Sheldon | 358/98 |
| 4,011,403 | 3/1977 | Epstein et al. | 358/209 |
| 4,170,997 | 10/1979 | Pinnow et al. | 128/395 |
| 4,418,688 | 12/1983 | Loeb | 128/6 |
| 4,418,689 | 12/1983 | Kanazawa | 128/6 |
| 4,419,987 | 12/1983 | Ogiu | 128/4 |
| 4,454,882 | 6/1984 | Takano | 128/395 |
| 4,473,841 | 9/1984 | Murakoshi et al. | 358/98 |
| 4,480,636 | 11/1984 | Karaki et al. | 128/6 |
| 4,550,240 | 10/1985 | Toida et al. | 128/4 |
| 4,562,831 | 1/1986 | Murakoshi et al. | 128/6 |
| 4,589,404 | 5/1986 | Barath et al. | 128/6 |
| 4,604,992 | 8/1986 | Sato | 128/6 |
| 4,641,650 | 2/1987 | Mok | 128/303.1 |
| 4,706,118 | 11/1987 | Kato et al. | 358/98 |
| 4,785,806 | 11/1988 | Deckelbaum | 128/303.1 |

FOREIGN PATENT DOCUMENTS

| | | | |
|---|---|---|---|
| 2821264 | 11/1978 | Fed. Rep. of Germany | 128/303.1 |
| 2821376 | 11/1978 | Fed. Rep. of Germany | 128/303.1 |
| 2829516 | 1/1980 | Fed. Rep. of Germany | 128/303.1 |
| 3245846 | 7/1983 | Fed. Rep. of Germany | 128/303.1 |

OTHER PUBLICATIONS

Ploem, Johan S., "Laser Scanning Fluorsecence Microscopy", Applied Optics, vol. 26, No. 16, Aug. 15, 1987, pp. 3226–3231.

Plesch, A., Klingbeil, U., and Bille, J., "Digital Laser Scanning Fundus Camera", Applied Optics, vol. 26, No. 8, Apr. 15, 1987, pp. 1480–1486.

Amos, W. B., White, J. G., and Fordham, M., "Use of Confocal Imaging in the Study of Biological Structures", Applied Optics; vol. 26, No. 16, Aug. 15, 1987, pp. 3239–3243.

*Primary Examiner*—Max Hindenburg
*Attorney, Agent, or Firm*—Chilton, Alix & Van Kirk

[57] ABSTRACT

An endoscope is adapted for operation in association with an optical scanner which generates a beam of radiation tracing out a raster. The endoscope employs at least one optical channel comprising a bundle of coherent flexible optical fibers. Elemental photodetectors which may be mounted at either the distal end of the endoscope probe or the proximal end of the endoscope probe are employed for sensing reflected radiation and generating a video signal. The optical channel may also be employed for transmission of a high-energy therapy beam. The endoscope is capable of obtaining multispectral-multidimensional (e.g. stereo) images of the tissue under examination.

10 Claims, 6 Drawing Sheets

ENDOSCOPE WITH TRACED RASTER AND ELEMENTAL PHOTODETECTORS

BACKGROUND OF THE INVENTION (1) Field of the Invention

This invention relates generally to endoscopes, which are employed in medicine for imaging selective body regions and for facilitating the delivery of high-energy radiation for treatment purposes. More particularly, the present invention relates generally to endoscopes which employ fiber optic channels and which employ lasers or other high-energy radiation sources.

(2) Prior Art and Pertinent Technology

The new and improved endoscope and associated system of the present invention has particular applicability in medicine for use as a gastroscope, sigmoidoscope, uretheroscope, laryngoscope, and bronchoscope. The invention also has applicability in connection with industrial applications, such as, for example, remote focus flexible fiberscopes, micro-borescopes, and microfiberscopes.

Conventional endoscopes typically employ incoherent bundles of optical fibers for transmitting light rays (typically white light) from a proximal end of a tubular instrument to the distal end. Typically, a pair of diametral channels are employed for illuminating an object to be imaged. A separate coherent flexible fiberoptic channel communicates from the distal end to the proximal end with an eyepiece, television camera, photographic camera or other imaging devices for providing an image. For relatively large diameter endoscopes, a separate flexible-fiber quartz channel may be employed for transmitting a high-powered beam of laser radiation to an object for therapeutic purposes. An auxiliary channel may traverse the tubular endoscope for receiving various instruments for severing and retrieving selected tissue. In addition, the endoscope may contain channels which provide for water and air communication with the distal end of the endoscope.

Conventional endoscopes provide a reasonably high quality image especially enlarged-diameter endoscopes. Conventional endoscopes are quite versatile and perform a large variety of useful functions. The conventional endoscopic optic systems, however, do exhibit a number of deficiencies. When viewing objects under high resolution, the image may exhibit a mesh or chicken-wire effect wherein individual groupings of fibers are outlined. Conventional endoscopes also exhibit some degree of loss of contrast associated with scatter intrinsic to the illumination of the object, and also some loss of contrast due to veiling glare of the multiple optical components. The space requirements, e.g., the diameter of the endoscope, represents a design constraint which is significant when separate illumination and imaging channels are employed. Such a constraint may be quite critical for vascular endoscopes which image interior arteries having diameters on the order of two millimeters or less. Another constraint of the conventional endoscopic optic systems is that they do not provide an optical system which facilitates stereo or three dimensional imaging, or the opportunity to acquire multispectral-multidimensional images, simultaneously.

The imaging channel of a conventional endoscope may be coupled to a television camera or the television camera may be employed in conjunction with an eyepiece by means of an optical beam splitter. The video signal output from the television camera is fed to a television monitor and/or a video recorder of a digital image acquisition system for processing, display and archival storage. The television camera may be a conventional television tube, a solid state video camera employing CCD chips, or other conventional forms.

Sato U.S. Pat. No. 4,604,992 discloses a CCD video camera chip at the distal end of the endoscope. The disposition of the CCD chip obviates the use of the coherent fiber optic bundle for imaging, and thus, provides a system which produces an image not susceptible to the chicken-wire effect or to individually broken fibers which cause pixel dropout. The size of the CCD chip, however, limits the minimal diameter of the endoscope. The CCD video camera chip also allows for the passage of high energy laser radiation to be trained on the object for therapy while the object is concurrently viewed through the CCD imaging camera.

Karaki et al U.S. Pat. No. 4,808,636 discloses a solid state type of imaging censor position at the proximal end of the endoscope. The analog video signal is converted to a digital signal. The digital signal is then processed to eliminate the chicken-wire or mesh effect and to account for the pixel dropout in the displayed image. Pixel dropout commonly results from broken fibers in the fiber optic bundle. The spacial resolution for the conventional endoscope is essentially determined by the diameter of the optical fibers and the magnification of the imaging optics. In general, the commonly employed fibers have diameters in the range of eight to ten microns for high-resolution endoscopes.

Other references which are related to the general field of the invention are identified by patentee and patent number as follows:

| | |
|---|---|
| Mok | U.S. Pat. No. 4,641,650 |
| Murakoshi and Yoshida | U.S. Pat. No. 4,473,841 |
| Murakoshi and Ando | U.S. Pat. No. 4,562,831 |
| Toida et al | U S. Pat. No. 4,550,240 |
| Pinnow and Gentile | U.S. Pat. No. 4,170,997 |
| Loeb | U.S. Pat. No. 4,418,688 |
| Kanazawa | U.S. Pat. No. 4,418,689 |
| Ogiu | U.S. Pat. No. 4,419,987 |
| Epstein and Mahric | U.S. Pat. No. 4,011,403 |
| Barath and Case | U.S. Pat. No. 4,589,404 |
| Kato et al | U.S. Pat. No. 4,706,118 |
| Takano | U.S. Pat. No. 4,545,882 |
| Sheldon | U.S. Pat. No. 3,499,107 |
| Sheldon | U.S. Pat. No. 3,021,834 |
| Sheldon | U.S. Pat. No. 2,922,844 |

SUMMARY OF THE INVENTION

Briefly stated, the invention in a preferred form, is a new and improved endoscope which incorporates a modified optical system for the endoscope, an optical scanner and an elemental detector-video system. The optical system is designed in one embodiment to employ a single coherent fiber-optic channel which can be used for both illumination and imaging. The endoscopic optical system, in conjunction with the optical scanner, permits acquiring images with improved contrast, improved spacial resolution, improved speed of response, the delivery of an independent beam of radiation directed precisely to a selected location of the object, multiple projection and multispectral imaging.

An endoscope in one embodiment comprises a bundle of coherent flexible optical fibers which form an optical channel. An elemental photodetector generates an electrical signal having an instantaneous value which is proportional to the quantity of light which impinges on the photodetector. The endoscope is adapted for operation in association with an optical scanner which generates a beam of radiation tracing out a raster. The raster from the scanner traverses a beam splitter and is projected on the proximal end of the optical channel. The raster light traverses the optical channel and is projected through the distal end of the optical channel for illuminating the surface of an object to be examined. Radiation reflected from the surface traverses back through the optical channel and is directed by the beam splitter to the photodetector. A high-energy therapy beam may also be projected on the proximal end of the optical channel for traversal through the channel. The photodetector may be selectively responsive to a preestablished narrow band of the electro magnetic spectrum.

In another embodiment, the endoscope comprises a bundle of coherent flexible optical fibers forming a first optical channel which extends the length of a flexible tubular probe. At least one incoherent flexible optical channel is received in the probe and diametrally spaced from the first optical channel for transmitting reflected optical radiation. Elemental photodetectors optically communicate with the incoherent optical channels and generate electrical signals having instantaneous values proportional to the quantity of light which impinges the photodetectors. Two incoherent optical channels may be provided and a photodetector associated with each incoherent optical channel forms a stereo pair of photodetectors to generate signals indicative of a stereo image of the surface of the object being examined.

In another embodiment, the endoscope has one coherent flexible fiber optical channel and at least one elemental photodetector is mounted at the distal end of the probe for sensing reflected radiation from the object under examination. The optical fibers of the optical channel may have the general shape of an elongated truncated cone wherein the diameter of the fibers at the proximal end of the cone is significantly greater than the diameter of the fibers at the distal end of the cone.

The proximal end surface of an optical channel may be defined by a substantially rigid connected bundle of fibers having a generally circular shape and the distal end surface of the optical channel may be defined by a rigid substantially connected bundle of fibers having a generally circular shape. The raster which is projected on the proximal end of the optical channel has a boundary which defines a central fiber region and an outer fiber region of the optical bundle. Photodetectors can be mounted for optical communication with optical fibers in the outer fiber region. Radiation reflected from the surface of the object being examined is transmitted through optical fibers of the outer fiber region, thereby permitting illumination and signal read out in a concentric manner.

An object of the invention is to provide a new and improved endoscope combined with a video laser scanner system therefor which does not require the need for a separate illumination channel.

Another object of the invention is to provide a new and improved endoscope which facilitates the use of stereo pairs and three-dimensional imaging of the surface to be illuminated.

A further object of the invention is to provide a new and improved endoscope having a compact and efficient form which is adapted for use with high-energy laser radiation.

A further object of the invention is to provide a new and improved endoscope and associated optical scanner system which is capable of imaging with one light or laser source while one or more other sources are employed simultaneously for therapy or other diagnostic purposes.

A further object of the invention is to provide multispectral with or without multidimensional imaging.

Other objects and advantages of the invention will become apparent from the drawings and the specification.

DETAILED DESCRIPTION OF THE INVENTION

Figure 1:
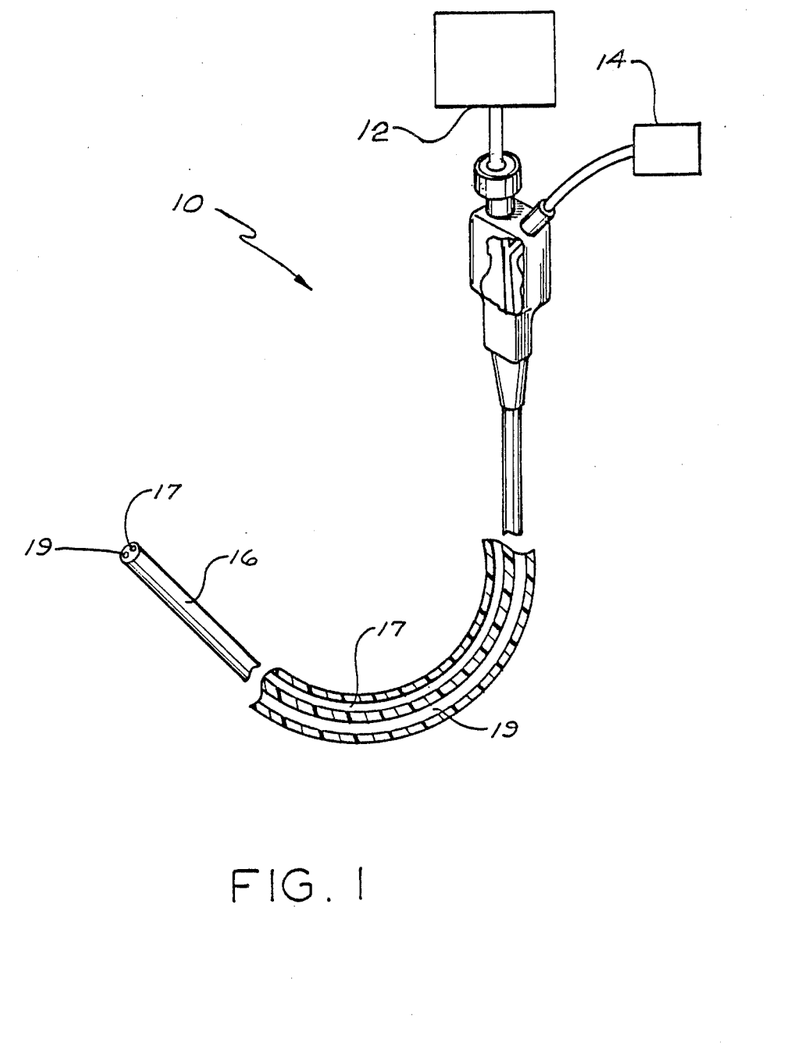
FIG. 1 is a side view, partly broken away and enlarged to show section and partly in schematic, illustrating a new and improved endoscope in accordance with the present invention.

With reference to the drawings wherein like numerals represent like elements throughout the figures, an endoscope in accordance with the present invention is generally designated by the numeral 10 in FIG. 1. A video optical scanner camera (schematically illustrated) designated generally by the numeral 12 is optically coupled to the endoscope. Scanner camera 12 contains a laser on a white light source. The endoscope 10 is especially adapted for use in conjunction with a video optical scanner camera which traces out a raster of illuminating light. The endoscope 10 has means for extracting a video signal 14 and an elongated flexible tubular probe 16 which is insertable into the body of a patient for examination and therapy purposes. The resulting endoscopic system, as will be hereinafter described, generates high speed, essentially lag-free images having a high resolution and wide dynamic range. The endoscopic system exhibits reduced scatter and reduced veiling glare and is adapted for spectral dependent tomography and multidimensional imaging including simple stereo projections. The endoscope probe 16 may be embodied in a relatively compact configuration which is dimensionally compatible with conventional, smaller diameter endoscopes. Probe 16 carries the coherent fiber optic channel 17. Another channel 19 of the probe might constitute a flexible tube through which a medical instrument, such as a biopsy tool can be passed.

Figure 3:
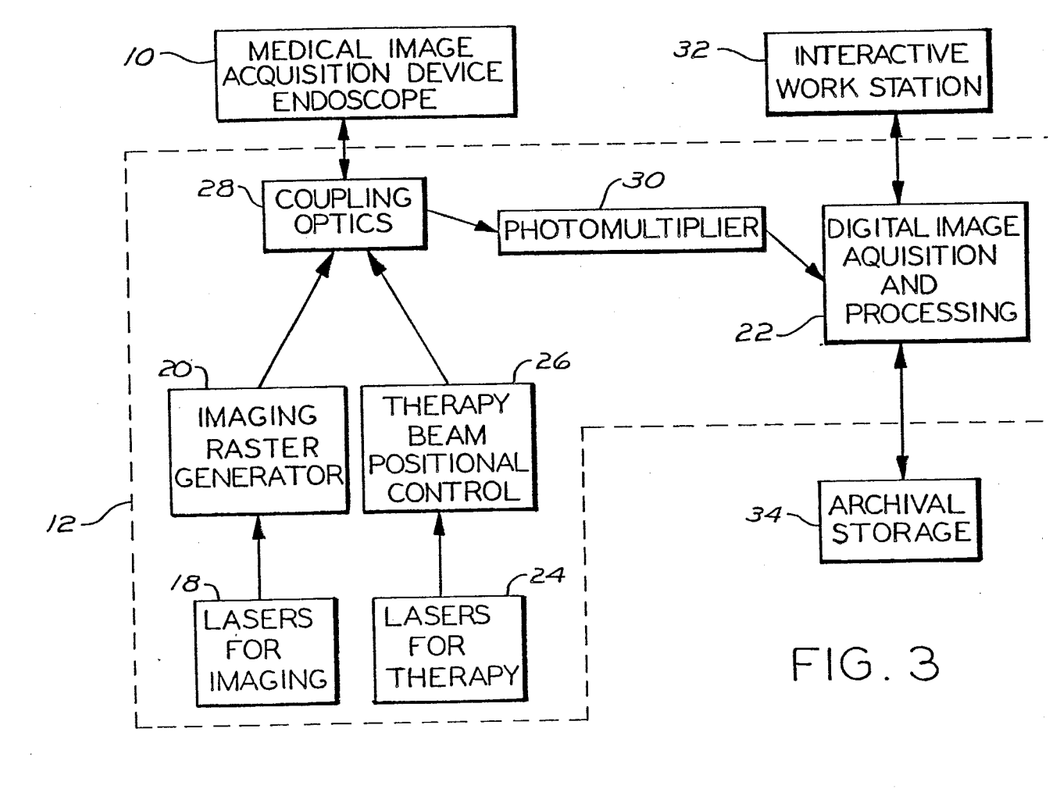
FIG. 3 is a schematic block diagram of the endoscope and the laser video camera system of FIG. 2.

With additional reference to FIG. 3, the video optical scanner camera 12 may be any of a number of conventional types. In preferred form, the camera 12 functions by projecting an optical raster of light onto the surface of an object. The camera senses the reflected radiation with an elemental photodetector to generate a video signal. Preferred cameras employ lasers 18 as a source of radiation although other non-laser sources can also be employed in connection with the invention. An associated raster generator 20 is optically coupled to laser 18 for generating an illuminating raster. As described herein, the invention is described in terms of a laser source of illumination for the object to be examined and imaged. The advantages of a laser source include a wide selection of laser lines, high optical efficiency, high energy generation for certain diagnostic and therapeutic procedures, well established relationships between the absorption of monochromatic lines and the identification of selected tissue and bones, and favorable reflection characteristics of selected lines for optimum contrast in obtaining an image.

The video laser camera (VLC) 12 preferably comprises a high resolution, wide dynamic-range digital video imager 22 providing optimal contrast. The VLC 12 also preferably includes lasers 24 and an associated laser beam control 26 capable of simultaneously delivering localized high-power laser radiation for therapy. The VLC 12 preferably avoids the loss of contrast from scattered radiation that exists when an object is illuminated with white light over its full surface during an exposure as characteristic of conventional photography or television. The VLC 12 illuminates an object locally as the laser scans through a raster with monochromatic radiation. Each raster pixel is recorded in succession. Consequently, the recorded pixel is not subject to the loss of contrast inherent in conventional video imaging which loss is principally due to radiation scattered from other pixels.

One suitable VLC 12 is a digital laser scanning fundus camera such as disclosed by A. Plesch et al, in an article entitled "Digital Laser Scanning Fundus Camera", *Journal of Applied Optics*, Apr. 15, 1987, Volume 26, No. 8. The latter VLC employs an air-cooled Ar-ion laser. The laser generates a beam passing through two microscopic objectives to shape the beam and to define a shutter. The raster generator comprises a polygon mirror scanner and a linear galvanometer scanner. The illuminating beam is horizontally deflected by an eighteen-face polygon mirror scanner rotating at approximately 52,100 rpm. The exit plane of the polygon scanner is projected on a scanning plane by a confocal arrangement of two camera lens systems and a General Scanning linear galvanometer. The scanner deflects the illuminating beam vertically with a repetition rate of 50 hertz on a fly-back time of 2 ms. A second symmetrical arrangement of two camera objective lenses projects the laser beam via a semi-transparent mirror of low reflectivity onto the surface of the object to be examined, e.g., the retina of the human eye.

Another suitable VLC 12 is an optical system such a disclosed by Johan S. Ploem in an article entitled, "Laser Scanning Florescence Microscopy", *Journal of Applied Optics*, Aug. 15, 1987, Volume 26, No. 16. The disclosed laser scanning system employs a laser beam which is expanded with a telescope to a size suitable for microscope objective lenses. The laser beam is displaced along two axes by an X-Y scanner unit consisting of two orthogonal galvanometer scanners. A pair of mirrors are interposed in the optical path. The beam is focused by a diffraction-limited spot on the object. Illuminated light is collected by the microscope condenser and directed to a photomultiplier tube. For florescence and reflectance microscopy applications, a light path retraces the entire illumination beam path in reverse, including the scanning mirrors, until the reflected beam is reflected by a beam splitter onto a photomultiplier tube. The disclosed confocal laser scanning microscopy provides for the imagery of multiple focal layers of the specimen and a three dimensional image reconstruction. Combinations of the images are stored in a computer memory for comparing phase contrast and florescence images of the same area of the specimen to enable multiparameter analysis of various cells.

Another suitable VLC 12 may be similar to the confocal microscope disclosed by W. B. Amos et al, in an article entitled, "Use of Confocal Imaging in the Study of Biological Structures", *Journal of Applied Optics*, Aug. 15, 1987, Volume 26, No. 16. Light passes from a laser into a reflector. The reflector is a chromatic reflector for florescence microscopy or a half-silvered mirror for reflection imaging. The optical scanning system directs a parallel beam of light into the eyepiece of a conventional microscope. The beam is focused to a diffraction-limited spot in the specimen. Light reflected or emitted by the specimen returns along the original illumination path and is separated from the incident light at the reflector.

A schematic block diagram of the principal components of a generalized VLC 12 and the endoscope 10 which comprise the overall endoscopic/camera system is illustrated in FIG. 3. The endoscope is bi-directionally optically coupled to the VLC by an optical coupler 28 which may comprise any of a number of optical components. The video signal from the endoscope returns via the optical coupler 28 and is applied to a photomultiplier 30 for transmission to the digital image acquisition and processing system 22. The acquisition and processing system 22 may be integrated into camera 12 or may be a separate unit. The video output signal from the camera may be transmitted to a work station 32. The work station 32 typically may be a console with interactive displays. The received video signals can be manipulated and studied by the diagnostician at the work station 32. The signals from the camera may also be cast into data form and transmitted to and from an archival storage 34.

It should be clear that the video signal from the photomultiplier can be fed to an analog display system for direct viewing when the image acquisition is in real time.

As will be further described hereinafter, the VLC and the endoscope cooperate to provide a system wherein, in addition to an imaging beam, a separate therapeutic laser beam generated by laser 24 of the camera is transmitted through the endoscope. The therapeutic beam is projected upon a selected location on the surface of the object or tissue under examination and the tissue is concurrently continuously monitored through the imaging optics system of the camera. The therapy beam can be precisely controlled by beam positional control 26 so that any localized region of the object being visually examined may be effectively treated without requiring repositioning of the probe end of the endoscope. In preferred form, the therapeutic laser 24 and the control 26 are integrated into the VLC 12. The VLC 12 can be configured to include as many lasers as required to provide a requisite monochromatic wavelength and power for illumination as well as therapy. The VLC can be employed for florescence imaging, i.e., with procedures where the incident radiation beam is in one wavelength and the imaging is accomplished with florescence radiation. The laser radiation, in some cases, can be employed when sufficient numbers of monochromatic lines are available in a manner similar to the illumination from a monochrometer with the system operating as a powerful scanning spectrophotometer. The VLC 12 also provides a high spacial resolution and a wide dynamic range, thereby permitting correlation between spacial features and spectral signatures.

Figure 2:
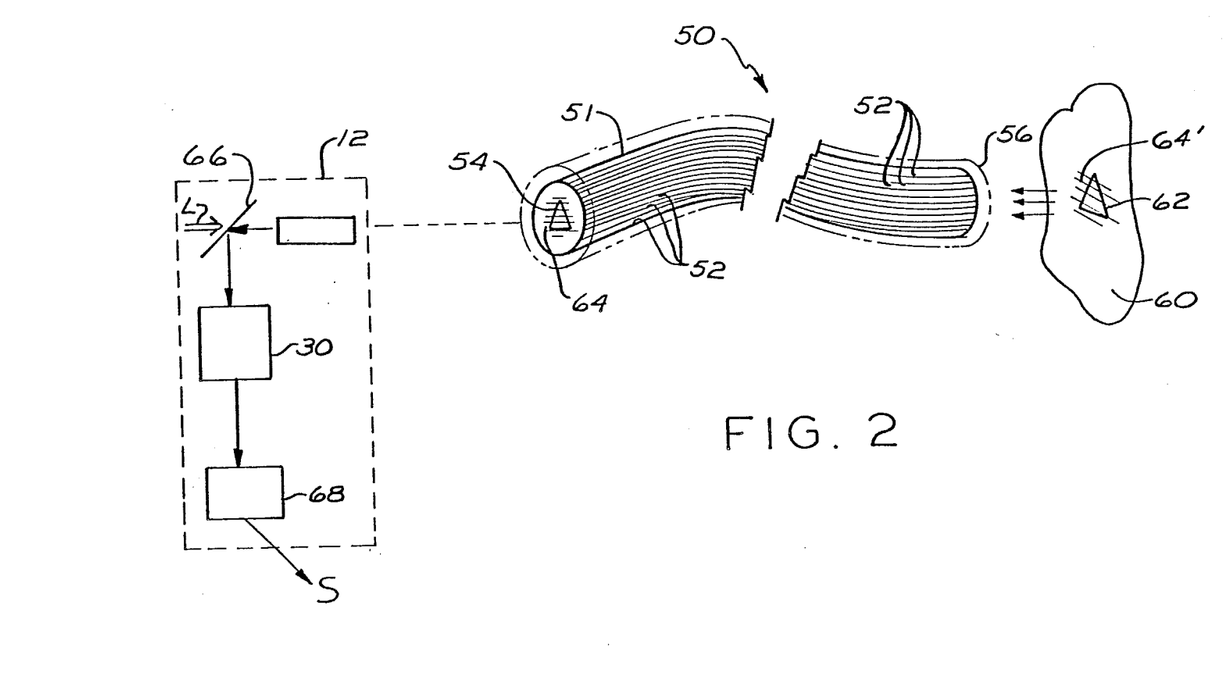
FIG. 2 is a schematic view illustrating the operation of the endoscope of FIG. 1 in conjunction with a video laser camera system in accordance with the present invention.

With reference to FIG. 2, one embodiment of an endoscope 10 comprises an elongated flexible tubular probe 50. Probe 50 is formed of flexible plastic, rubber or other conventional materials. A flexible coherent fiber optics bundle 51 comprising a multiplicity of optical fibers 52 traverses the length of the probe from the proximal end 54 to the distal probe end 56. In the region adjacent to the proximal and distal ends, the coherent fiber bundle 51 is essentially rigid. The fibers 52 at the bundle ends are fused into the shape of a solid small cylindrical segment so that the individual fibers 52 of the bundle maintain their spacial relationship or coherency.

The probe 50 is illustrated in relation to a body or tissue section 60 to be examined. The distal end 56 of the probe is positioned in close proximity to tissue section 60 by conventional means. The specific object (illustrated as a triangle) of the body section which is to be imaged by the endoscope is designated by the numeral 62. Monochromatic illumination light (L) from a laser raster scanner impinges a beam splitter 66 of a camera 12 for projecting an input raster 64 from the laser scanner onto the proximal end 54 of the probe 50. The light traverses the fiber optics bundle 51 of the probe and is projected through the distal end 56 so as to trace a raster 64' onto the surface of the object 62 to be examined. The raster light scans over the surface of the object in a serial fashion.

Reflected light from the object 62 returns in the direction of the FIG. 2 arrows through the fiber optics bundle and strikes the beam splitter 66 of camera 12. The reflected light is sensed by a photomultiplier 30 whose output is fed to a video amplifier 68. The amplifier 68 transmits an electrical video signal(s), which at a given instant of time, is proportional to the quantity of light reflected from the point on the surface of the object 62 to which the laser beam raster is projected. The electronic video signal can then be transmitted to an analog system for recording and display or to a digital imaging system for recording, processing and display.

The latter described endoscope essentially employs a single fiber optics channel and does not require separate illumination and imaging channels. Moreover, by integrating the endoscope optical paths of the therapy laser beam with the imaging laser beam, the requirement of a separate therapeutic channel to carry high-powered laser radiation may also be eliminated. Consequently, the endoscope comprising probe 50 has particular applicability in connection with endoscopes for very small diameter applications such as required in the imaging of coronary arteries. Many of the conventional problems associated with high-powered light requirements are solved by lasers having a sufficient power to provide the selected monochromatic radiation to thereby operate in a far more efficient manner than conventional light sources. An additional advantage of the endoscope lies in the scatter reduction and the contrast improvement which is realized by recording the reflected radiation from successive localized pixels imaged as the beam serially progresses through a raster. The raster scanning process avoids the inherent problem of contrast loss through scatter that ordinarily prevails when illuminating the entire surface of an object and recording the image at the same time. In conventional endoscope optic systems, scattered radiation from one pixel is commonly detected in another imaged pixel to thereby reduce the intrinsic imaging signal. In addition, antireflection coatings can be applied to the optical fibers with a high degree of precision. The coatings minimize loss of contrast with a scanner employing monochromatic radiation compared to loss of contrast with a scanner employing a customary white light source. Consequently, the endoscope of FIG. 2 is particularly advantageous for applications wherein an image may be suitably observed by illumination of a single monochromatic laser line.

Figure 4:
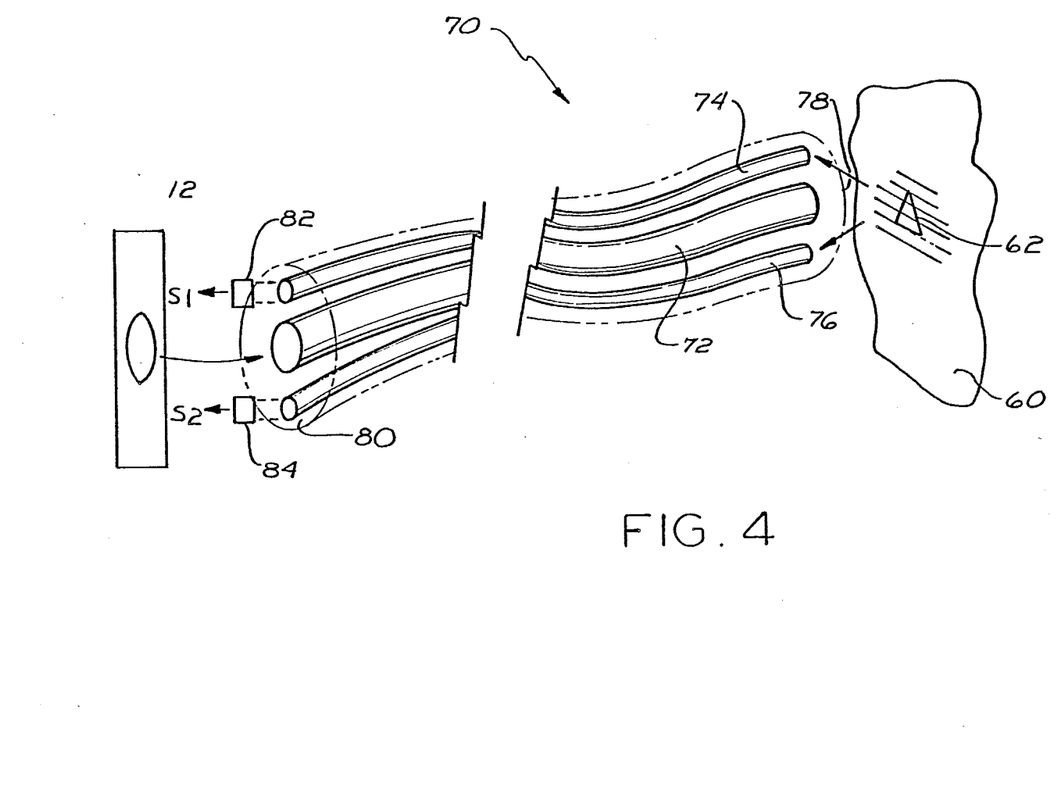
FIG. 4 is a schematic view of a second embodiment of an endoscope and an associated optical system in accordance with the present invention.

With reference to FIG. 4, the endoscope probe 70 has a central flexible fiber optic bundle 72 for raster illumination of the object 62 of tissue to be examined. A pair of diametrically opposed light channels 74 and 76 of optical fibers extend longitudinally parallel to bundle 72 to transmit the reflected radiation from the object 62 along an optical path extending from the distal probe end 78 to the proximal end 80 of the endoscope. Photodetectors 82 and 84 are positioned at the proximal ends of the light channels 74 and 76, respectively. The reflected radiation transmitted through the light channels impinges the photodetectors 82 and 84. The photodetectors 82 and 84 in turn generate electrical video signals $S_1$ and $S_2$ for processing as previously described.

The monochromatic light from the laser raster scanner 20 and laser therapy positioner 26 is applied at the proximal end 80 of the fiber optics bundle 72. The endoscope of FIG. 4 does not employ a beam splitter. Consequently, reflections from the proximal input surface of the fiber optics bundle 72 are minimized. Reflections are also encountered in connection with beam splitters. In addition, the problem of veiling glare associated with multiple optical components in an imaging chain may also be substantially reduced by the elimination of the beam splitter. Short time constant photo- detectors are preferably employed so that the time lag characteristic which conventionally prevails in conventional endoscopic optical systems using video tubes is avoided.

Because two detector illumination channels 74 and 76 are employed with each illumination channel having its own photo-detectors 82 and 84, two images in the form of signals $S_1$ and $S_2$ can be acquired independently. The channels can thus be combined to form a stereo pair. Alternatively, the images acquired may be from two widely separated spectral regions, such as the UV and IR, if desired.

Figure 5:
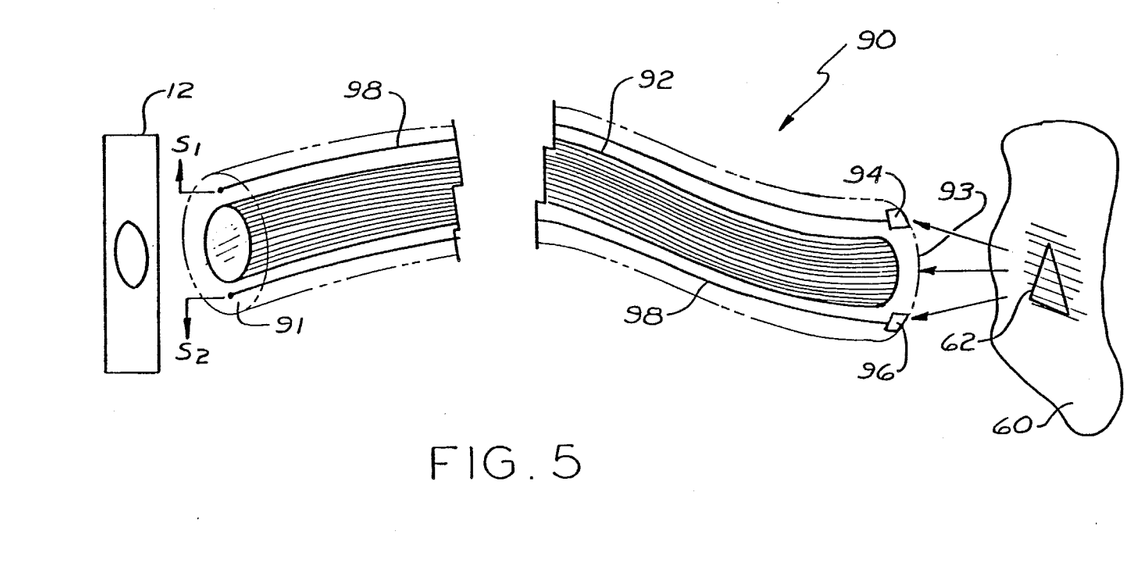
FIG. 5 is a schematic view of a third embodiment of an endoscope and an associated optical system in accordance with the present invention.

With reference to FIG. 5, endoscope probe 90 has a central coherent fiber optics bundle 92 which extends longitudinally from the proximal end 91 to the distal end 93. The fiber optics bundle 92 functions as previously described to project a video raster 64, onto the object 62 to be examined. Elemental photodetectors 94 and 96 are mounted at the distal probe end 93 of the endoscope for detecting incident reflected radiation from the object 62. Wires 98 extend the length of the endoscope for carrying the electrical bias and the signal current from the elemental photodetectors 94 and 96. The electrical video signals $S_1$ and $S_2$ communicate via the electrical wires 98 with the circuitry for processing the video signal.

It should be appreciated that endoscope probe 90 does not require separate optical detector and illumination channels since the elemental photodetectors 94 and 96 are located at the distal end 93 of the endoscope. As the illumination beam scans out a raster, the video signal is generated in a highly efficient manner since the photodetectors are positioned in an optimal location in the immediate vicinity of the object 62 to be examined. The photodetectors 94 and 96 may be relatively small in dimensions. Thus, the diameter of the endoscope probe 90 may be relatively small. One or more stereo pairs of images may also be obtained. Several photodetectors may be positioned at the distal end of the probe. The photodetectors may be configured into shapes which are circular, square, rectangular, polygonal, or other shapes as desired.

An endoscope comprising probe 90 avoids the loss of optical transmission through the illumination channels. Quartz fibers typically provide optical transmission throughout the spectrum range for a wide variety of applications between 3,000 Angstroms and 2 microns. The elemental photodetectors can be selected so as to operate in the spectral range from 3,000 to 20,000 Angstroms. One or more small photodetectors can be selected and suitably positioned at the distal probe surface of the endoscope to specifically respond to whatever radiation is selected for the imaging and therapy, regardless of the wavelength of the reflected radiation. It should be appreciated that a given endoscope, as described, is suitable for UV imaging as well as for imaging at two microns. The endoscope probe 90 offers wide range of spectral response. For example, signal $S_1$ may be responsive to reflected radiation imaging in one given spectral region and signal $S_2$ may be responsive to reflected laser therapy radiation in another spectral region. Endoscope probe 90 is also adaptable for multispectral imaging for contrast enhancement for a given endoscope.

Photodetectors 94 and 96 which are suitable for the described endoscope can be fabricated from materials such as crystalline silicon, amorphous silicon, cadmium sulfide and lead sulfide. For operation in the ultra-violet through the visible spectrum, into the near infra-red, the photodetectors as described provide extremely reliable performance at body or room temperatures. Combinations of infra-red transmitting fiber and cooled photodetectors may also be employed for infra-red applications. Uncooled thermal detectors which offer less performance may be satisfactory for some infra-red applications.

The laser camera system, as described, may function as an imaging scanner spectrophotometer by using one or more photo-detectors with their spectral responses matched to that required for the given spectrum encompassed in an application. The relative spectral reflectance for each pixel in an image can be measured for a given imaging radiation. By precise calibration, absolute reflectance values can be obtained.

The laser therapy can be effectively accomplished with the described video laser camera systems and endoscopes. If a given laser line is best suited for a given therapy, the laser line can be transmitted through one or more of the fibers to the object requiring treatment. The number of selected fibers defines the composite therapy beam diameter. For example, if a lesion on the surface of the object is imaged by ten to twenty fibers, then the laser radiation for therapy could be channeled through the same fibers of bundle 92 to cover the designated lesion area. Simultaneous imaging may also be accomplished through the same fibers consistent with the raster scanner operation. The high-powered therapeutic radiation generated by laser 24 can be shuttled back and forth through the fiber optic bundles or even pulsed through one or more fibers to minimize the heating problems. Heating, in general, is ordinarily not a critical problem, since high-temperature glass fibers have been developed which operate at temperatures up to 800° Fahrenheit. Quartz fibers have an even higher temperature operational limit.

For the described endoscopic systems, there are two principal operational techniques wherein the high-energy therapy irradiation of an object can be accomplished simultaneously with viewing the reaction of the object to the irradiation treatment. In one technique, both the imaging beam and high-energy therapy beam pass through the scanning system. Such an approach requires that the high-energy therapy beam be pulsed in synchronization with the scanning raster so that the high-energy therapy beam is delivered in a precise manner. The first approach requires that the precise timing of the imaging pulses and therapeutic laser pulses be coordinated.

In a second technique, the high-energy irradiation is transmitted by a second separate optical system. This second general approach does not require the pulsing of the therapeutic beam and synchronization of the scanning of the raster. However, the imaging channels might need to be filtered so that the high energy irradiation does not interfere with the imaging process. Consequently, photo-detectors employed in such a system could require sufficient filtering so that the photodetectors selectively respond only to radiation from the low-energy imaging beam. For endoscope probes 70 and 90, which employ multiple detectors, one or more of the photodetectors may be employed to sense (view) the imaging radiation while being opaque (blind) to the high-energy radiation. By the proper selection of the photodetector and the filter, detectors may be employed to monitor the level of reflected radiation with time as the high-energy therapy beam causes a change in the reflectance properties of the object or tissue on which the high-energy beam is focused.

It should be noted that the use of multiple-elemental detectors, which are each capable of providing an independent image of the object from a different viewing angle, makes possible stereo imaging. Any such pair of the images (electrical signals) essentially can be electronically coupled to constitute a stereo pair. One or more elemental detectors positioned at different viewing angles relative to the object result in the images being multiply-generated to obtain the optimal stereo view of an object. In addition, spectral selective viewing of a structure below an object surface can be obtained since the images obtained from different laser wavelengths can in certain cases represent different depths of penetration below the surface of an object. Tomographic planes may thus be constructed.

Contrast enhancement can also be obtained by multispectral imaging. The multi-spectral imaging is accomplished by means of employing photodetectors having different defined spectral responses. Processing of the electrical video signals may be accomplished by means of energy subtraction techniques such as are employed in digital radiology and red-near infra-red subtraction techniques employed in diaphranography of the breast.

Figure 6:
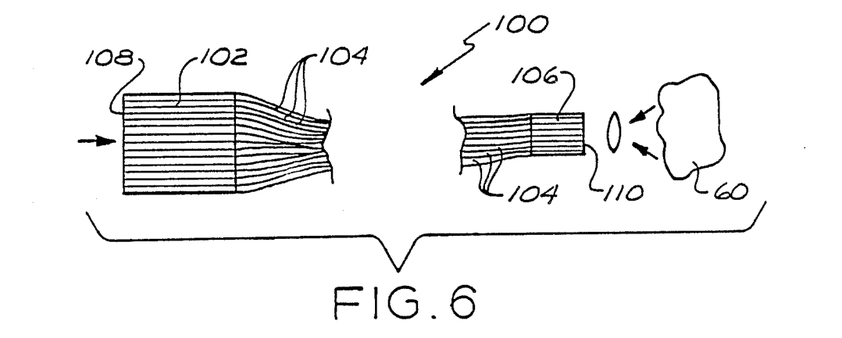
FIG. 6 is a fragmentary side view, partly in schematic, illustrating a fiber optic bundle for an endoscope in accordance with the present invention.

With reference to FIG. 6, one embodiment of a rigid coherent fiber optics bundle 100 for an endoscope as previously described comprises a proximal cylinder 102 consisting fused strands of substantially identical optical fibers 104. Likewise, a distal cylinder 106 comprising fused strands of the fibers is formed at the distal end of the endoscope. The diameters of the fibers at the proximal cylinder 102 are significantly larger than the associated corresponding optical fiber diameters of the distal cylinder. The optical fibers 104 may have a substantially constant taper from the proximal to distal ends. Thus, the individual fibers 104 may be described as elongated truncated cones.

Monochromatic light from the laser raster scanner is applied at the input surface 108 of the proximal cylinder 102. The relatively large input surface 108 defined by the proximal end of the fibers 104 functions to provide large heat capacity, means for cooling and a better ability to withstand damage from intense laser radiation, at optics bundle 100. In conventional endoscopes, high-energy laser radiation frequently does often result in fiber damage, particularly at the proximal end of the endoscope fibers. Because the flexible optical fibers are selected to be highly transmissive, the fibers are not particularly subject to appreciable increases in temperature unless there are localized impurities. However, the proximal cylinder 102 is susceptible to damage in large part because of the high absorption in the cladding material which leads to excessively high temperature and damage from thermal shock. By constructing the fiber diameters at the input surface 108 to be much larger than the fiber diameters at the output surface 110, the potential for thermal shock can be diminished. Thus, all other relevant physical characteristics of bundle 100 being equal, the energy density of a laser beam transmitted through fiber bundle 100 could be considerably increased and the heat capacity input considerably increased while decreasing the potential damage to the fiber optics bundle. For example, for a bundle 100 where the diameter of the input surface 108 to the output surface 110 is 10 to 1 a 10 micron flexible fiber optic bundle could have an effective input of 100 microns.

Figure 7:
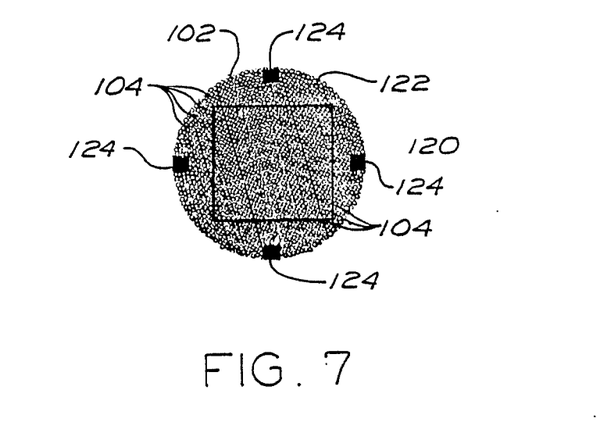
FIG. 7 is an enlarged end view of the endoscope proximal optic bundle (cylinder) of FIG. 6.

For procedures which involve multi-spectral imaging, surface tomography, different spectral responses and different perspectives, multiple detectors may be required. Such detectors may be efficiently arranged and mounted at the proximal end or region of the fiber optics bundle as illustrated in FIG. 7. For the configuration illustrated in FIG. 7, boundary 120 (schematically illustrated) of the raster which is projected onto the proximal cylinder encompasses only a central portion of the entire cross-sectional extent of the fiber optics bundle. Accordingly, an outer ring 122 of fibers are available for coupling to the photodetectors 124. Essentially, the central raster illumination transmission zone, defined by boundary 120, is encircled by a concentric ring 122 of fiber channels. The fibers in the ring 122 can be employed, either individually or collectively in groups, to transmit the reflected radiation from the tissue surface illuminated by the laser radiation near the distal end of the endoscope probe back to the photodetectors 124, which are located at the proximal end.

In one example, the diameter of the input proximal end 108 of the fiber optic bundle 100 is four millimeters, and the diameter at the distal probe end 110 is one millimeter. The effective demagnification of the fiber optics bundle 100 is approximately four. An individual fiber at the proximal end having a diameter of 40 microns has a corresponding diameter at the distal end of 10 microns. If laser raster defined by a square boundary 120 having a diagonal dimension of two millimeters is centrally projected on the proximal surface 108, a one millimeter thick ring 122 of fibers remain to function as the optical channels for photodetection. Such a ring could accommodate twelve detectors 124 in side-by-side orientation having dimensions of approximately one-by-one millimeter. The specific shape and dimensions of the detectors 124 could be suitably varied in accordance with the requirements of a specific application.

A laser raster scanner system as described can be employed in conjunction with multiple photodetectors to provide multi-spectral imaging. For example, an Nd:YAG laser which generates the typical line at 1.064 microns and a strong line at 1.318 microns can be coupled to different elemental photodetectors. Each of the elemental photodetectors is responsive to one of the laser lines so that the object under examination can be imaged simultaneously with both lines. For example, a laser system, such as described by R. A. Morgan, "Nd:YAG Laser For the Study and Application of Non-Linear Optical Chrystals", *Optical Engineering*, Volume 26, Pages 1240–1244, 1987, when suitably coupled with non-linear optical crystals, can permit simultaneous generation of frequencies extending throughout the visible spectrum, including the three primary colors and into the near ultra-violet range.

While preferred embodiments of the invention have been set forth for purposes of illustration, the foregoing description should not be deemed a limitation of the invention herein. Accordingly, various modifications, adaptations and alternatives may occur to one skilled in the art without departing from the spirit and the scope of the present invention.

What is claimed is:

1. An endoscope adapted for operation in association with an optical scanner which generates a beam of radiation tracing out a raster comprising:
    probe means for forming an elongated flexible endoscopic tube having a proximal end and a distal end;
    an optical channel enclosed in said probe means comprising a bundle of coherent optical fibers extending from a channel proximal end to a channel distal end;
    at least one elemental photodetector mounted at the distal end of said probe means;
    electrical wire means for providing electrical communication between said at least one photodetector and the proximal end of said probe means,
    so that a raster from said scanner projected on said proximal end of said optical channel traverses said channel and is projected through said optical channel distal end for illumination of the surface of an object to be examined and reflected radiation from said surface is sensed by said at least one photodetector which generates a corresponding electrical signal for transmission through said electrical wire means.

2. The endoscope of claim 1 wherein at least one photodetector is only responsive to a pre-selected region of the electromagnetic spectrum.

3. The endoscope of claim 1 wherein said optical channel and said photodetectors are operational over an electromagnetic spectrum extending from the ultra-violet to the infra-red ranges.

4. The endoscope of claim 1 wherein the optical fibers of said optical channel have the general shape of an elongated truncated cone, the diameter of the fibers at said proximal end being significantly greater than the diameter of the fibers at said distal end.

5. The endoscope of claim 1 further comprising cooling means for cooling the optical fibers in the region of the proximal end.

6. The endoscope of claim 1 wherein there are two photodetectors.

7. The endoscope of claim 1 wherein there are a plurality of photodetectors generally equiangularly positioned at the distal end of said endoscope.

8. The endoscope of claim 1 further comprising digital image acquisition and processing means coupled to said wire means for converting said signals to digital data and processing said data to form a visual image.

9. The endoscope of claim 1 further comprising an optical scanner means for generating a beam of radiation tracing out a raster and means for projecting said raster at a proximal end of said optical channel.

10. The endoscope of claim 9 further comprising a plurality of photodetectors each of which are responsive to different pre-selected regions of the electromagnetic spectrum.

* * * * *